(12) United States Patent
Oonishi (10) Patent No.: US 12,233,287 B2
(45) Date of Patent: Feb. 25, 2025

(54) PARTICLE BEAM TREATMENT APPARATUS

(71) Applicant: SUMITOMO HEAVY INDUSTRIES, LTD., Tokyo (JP)

(72) Inventor: Teruaki Oonishi, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 108 days.

(21) Appl. No.: 17/679,340

(22) Filed: Feb. 24, 2022

(65) Prior Publication Data

US 2022/0266062 A1 Aug. 25, 2022

(30) Foreign Application Priority Data

Feb. 25, 2021 (JP) .................................. 2021-028634

(51) Int. Cl.
*A61N 5/10* (2006.01)

(52) U.S. Cl.
CPC ......... *A61N 5/1081* (2013.01); *A61N 5/1048* (2013.01)

(58) Field of Classification Search
None
See application file for complete search history.

(56) References Cited

U.S. PATENT DOCUMENTS

| | | | |
|---|---|---|---|
| 4,917,344 A * | 4/1990 | Prechter | F16C 19/507 |
| | | | 250/492.3 |
| 8,880,250 B2 | 11/2014 | Wu et al. | |
| 9,475,403 B2 | 10/2016 | Wu et al. | |
| 2018/0264290 A1* | 9/2018 | Hassan | H05H 7/001 |
| 2019/0001157 A1* | 1/2019 | Stacey | A61N 5/1081 |
| 2019/0151677 A1* | 5/2019 | Jongen | A61N 5/1081 |
| 2023/0052335 A1* | 2/2023 | Jiang | A61N 5/1081 |

FOREIGN PATENT DOCUMENTS

| | | | |
|---|---|---|---|
| KR | 101796512 B1 * | 11/2017 | ........... A61N 5/1081 |
| WO | WO-2012/118589 A1 | 9/2012 | |

* cited by examiner

*Primary Examiner* — Marcus H Taningco
(74) *Attorney, Agent, or Firm* — Michael Best & Friedrich LLP (57) ABSTRACT

A particle beam treatment apparatus that irradiates an irradiation target with a particle beam includes: a hollow rotary shaft including a hollow portion; an electromagnet that controls the particle beam in the hollow portion, the rotary shaft being rotatable by a power source; and a support portion that rotatably supports the rotary shaft, the rotary shaft including a first opening portion, the hollow portion being accessible to a worker through the first opening portion.

14 Claims, 7 Drawing Sheets

PARTICLE BEAM TREATMENT APPARATUS

RELATED APPLICATIONS

The content of Japanese Patent Application No. 2021-028634, on the basis of which priority benefits are claimed in an accompanying application data sheet, is in its entirety incorporated herein by reference.

BACKGROUND

Technical Field

Certain embodiments of the present invention relate to a particle beam treatment apparatus.

Description of Related Art

Conventionally, as a particle beam treatment apparatus that performs treatment by irradiating an affected part of a patient with a particle beam, for example, an apparatus of the related art is known. In the particle beam treatment apparatus of the related art, a particle beam accelerated by an accelerator is emitted from an irradiator.

SUMMARY

According to an embodiment of the present invention, there is provided a particle beam treatment apparatus that irradiates an irradiation target with a particle beam, the apparatus including: a rotary shaft including a hollow portion; an electromagnet that controls the particle beam in the hollow portion, the rotary shaft being rotatable by a power source; and a support portion that rotatably supports the rotary shaft, the rotary shaft including a first opening portion, the hollow portion being accessible to a worker through the first opening portion.

DETAILED DESCRIPTION

When the particle beam is emitted from the irradiator, there is a case where a rotating gantry that is used to rotate the irradiator is provided in order to perform irradiation from various angles. Here, electromagnets that are used to control the focusing of the particle beam or to control the direction of the particle beam are provided inside the rotating gantry. The electromagnets are provided at hard-to-access positions for a worker because the electromagnets are stored inside a rotary shaft. Therefore, there is a problem that the maintenability of the electromagnet is low in a case of, for example, periodic inspection or abnormality.

In that regard, it is desirable to provide a particle beam treatment apparatus capable of improving the maintenability of an electromagnet in a rotary shaft.

The particle beam treatment apparatus includes the rotary shaft including a hollow portion, and the electromagnet that controls the particle beam in the hollow portion, the rotary shaft being rotatable by the power source. Since the rotary shaft has a hollow structure, a space of a predetermined size is provided in the hollow portion of the rotary shaft. Therefore, the electromagnet can be disposed in the space provided in the hollow portion of the rotary shaft. The rotary shaft includes the first opening portion. The hollow portion is accessible to the worker through the first opening portion. Therefore, the hollow portion is accessible to the worker through the first opening portion to allow the worker to perform maintenance of the electromagnet in the space secured in the hollow portion of the rotary shaft. Consequently, the maintenability of the electromagnet in the rotary shaft can be improved.

The rotary shaft may have a monocoque structure. In this case, a wider space in the hollow portion of the rotary shaft can be secured as compared with the rotary shaft of a frame structure or the like. In addition, it is easier to form the first opening portion with respect to the rotary shaft.

The support portion may include a housing that accommodates the rotary shaft, the housing including a second opening portion, the hollow portion being accessible to the worker through the first opening portion and the second opening portion. In this case, the worker passes through the second opening portion even in a case where the housing is provided on the outer side of the rotary shaft, whereby the hollow portion is accessible to the worker.

The support portion may include roller members that apply a rotation driving force to the rotary shaft. In this case, bearings may not necessarily be provided for the rotary shaft. Accordingly, it is possible to omit the housing. Consequently, it is possible to restrain a structure from being provided around the rotary shaft, so that the hollow portion is easily accessed.

The particle beam treatment apparatus may further include a cable accommodation body that accommodates a cable connected to the electromagnet, in which the cable accommodation body may be attached so as to be windable around the rotary shaft, and may be drawn out of one side of the rotary shaft when viewed from an axial direction in which a center line of the rotary shaft extends. In this case, the rotary shaft is set to have a specific rotation angle, so that it is possible to avoid the cable accommodation body to access the hollow portion.

The support portion may include a housing that accommodates the rotary shaft, and a second opening portion may be formed in the housing on a side opposite to a draw-out side of the cable accommodation body when viewed from the axial direction. In this case, the hollow portion is easily accessible from the side opposite to the draw-out side of the cable accommodation body through the second opening portion.

The first opening portion is provided on one end side in a direction along the rotary shaft. In this case, the hollow portion is accessible to the worker from the one end side of the rotary shaft to allow the worker to perform maintenance of the electromagnet.

The particle beam treatment apparatus may further include a bearing provided on the one end side of the rotary shaft, the hollow portion being accessible to a worker through an inner peripheral side of the bearing. The rotary shaft is supported by using the bearing in which a large space is provided on the inner peripheral side, so that the support structure on the one end side of the rotary shaft can restrain the opening from being blocked. With this, the hollow portion is accessible to the worker from the inner peripheral side of the bearing without the obstruction of the passage.

The particle beam treatment apparatus may further include an irradiator that irradiates the irradiation target with the particle beam; and a support frame that supports the irradiator, in which a counterweight may be provided on a side of the support frame. In this case, since the counterweight is disposed at a position that does not obstruct the worker's access to the hollow portion, the hollow portion is easily accessed.

According to the present invention, it is possible to provide a particle beam treatment apparatus capable of improving the maintenability of an electromagnet in a rotary shaft.

Hereinafter, preferred embodiments of the present invention will be described in detail with reference to the accompanying drawings. In the following description, the same or corresponding portions are designated by the same reference numerals, and duplicate description will not be repeated.

Figure 1:
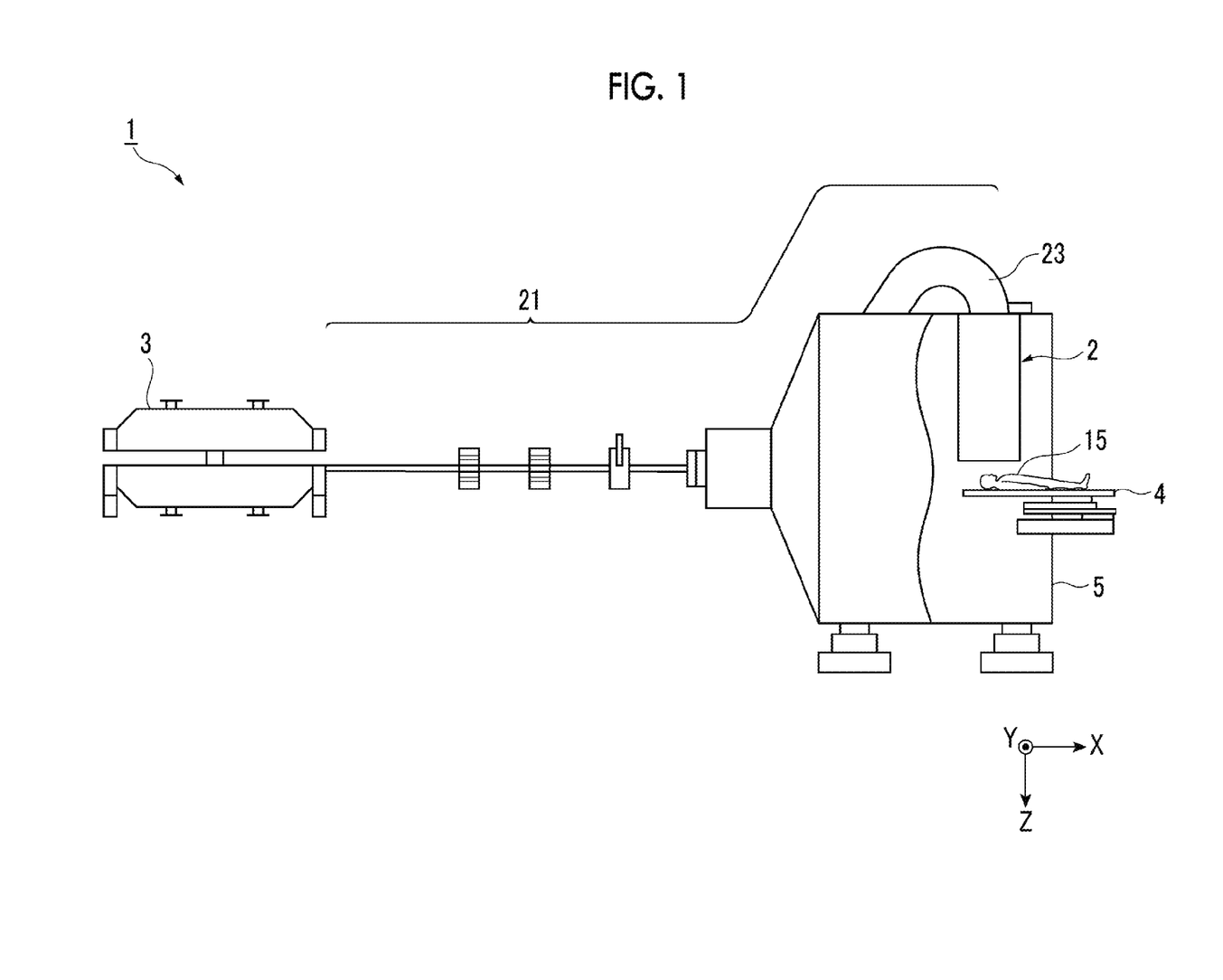
FIG. 1 is a schematic configuration view showing a particle beam treatment apparatus according to an embodiment of the present invention.

FIG. 1 is a schematic configuration view showing a particle beam treatment apparatus 1 according to an embodiment of the present invention. The particle beam treatment apparatus 1 is an apparatus that is used for cancer treatment or the like by radiation treatment. The particle beam treatment apparatus 1 includes an accelerator 3 that accelerates charged particles generated by an ion source apparatus and that emits the charged particles as a particle beam, an irradiator 2 that irradiates an irradiation target with the particle beam, and a beam transport line 21 that transports the particle beam emitted from the accelerator 3 to the irradiator 2.

The irradiator 2 is attached to a rotating gantry 5 provided so as to surround a treatment table 4. The irradiator 2 is made rotatable around the treatment table 4 by the rotating gantry 5. The beam transport line 21 enters the rotating gantry 5 from the rear end side of the rotating gantry 5. Then, the beam transport line 21 changes the trajectory of the particle beam to the outer peripheral side by a bending electromagnet 22 (see FIG. 3) and then greatly bends the trajectory of the particle beam by a bending electromagnet 23 to enter the irradiator 2 from the outer peripheral side.

Figure 2:
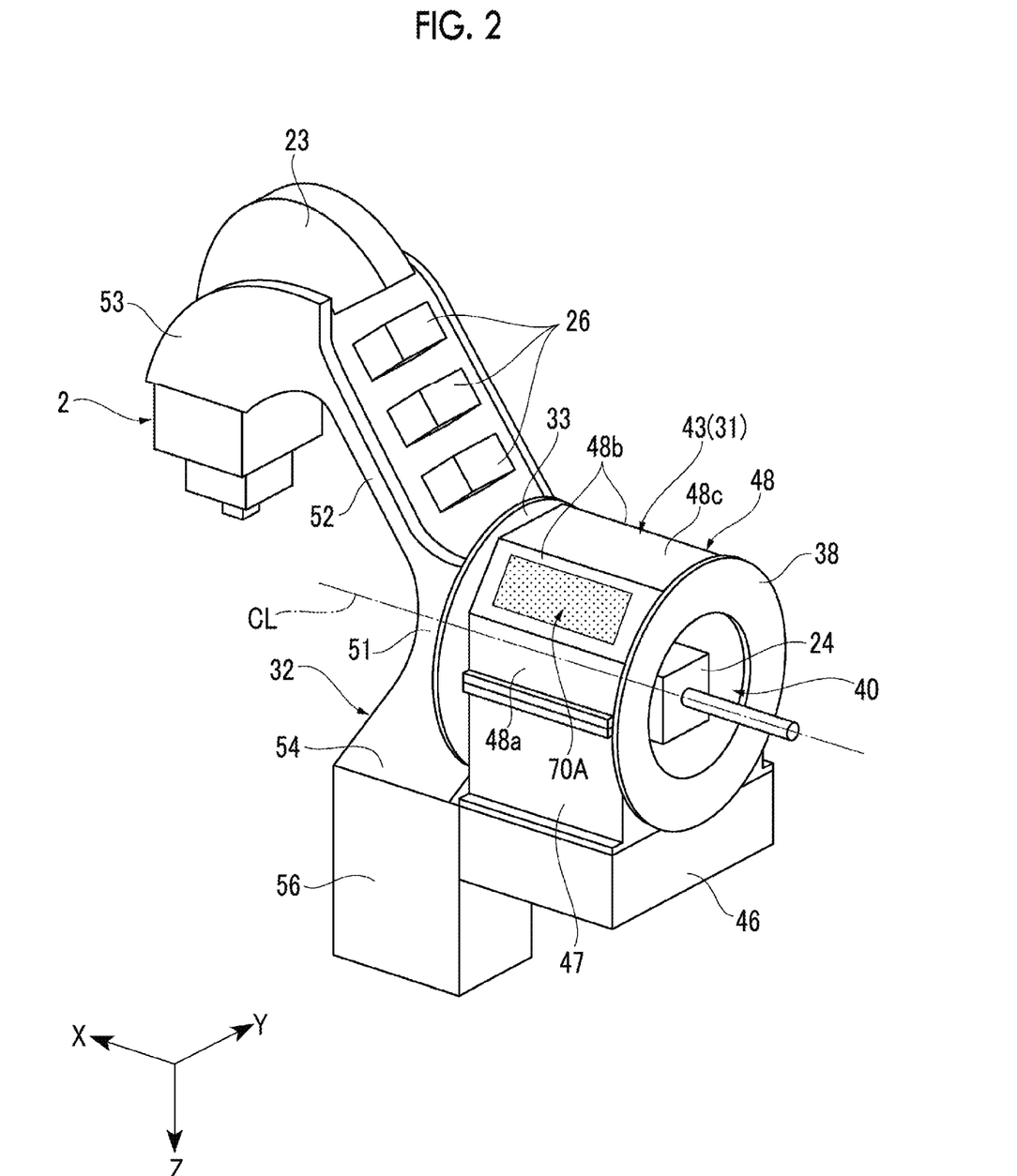
FIG. 2 is a schematic perspective view of the vicinity of a rotating gantry of the particle beam treatment apparatus.
Figure 3:
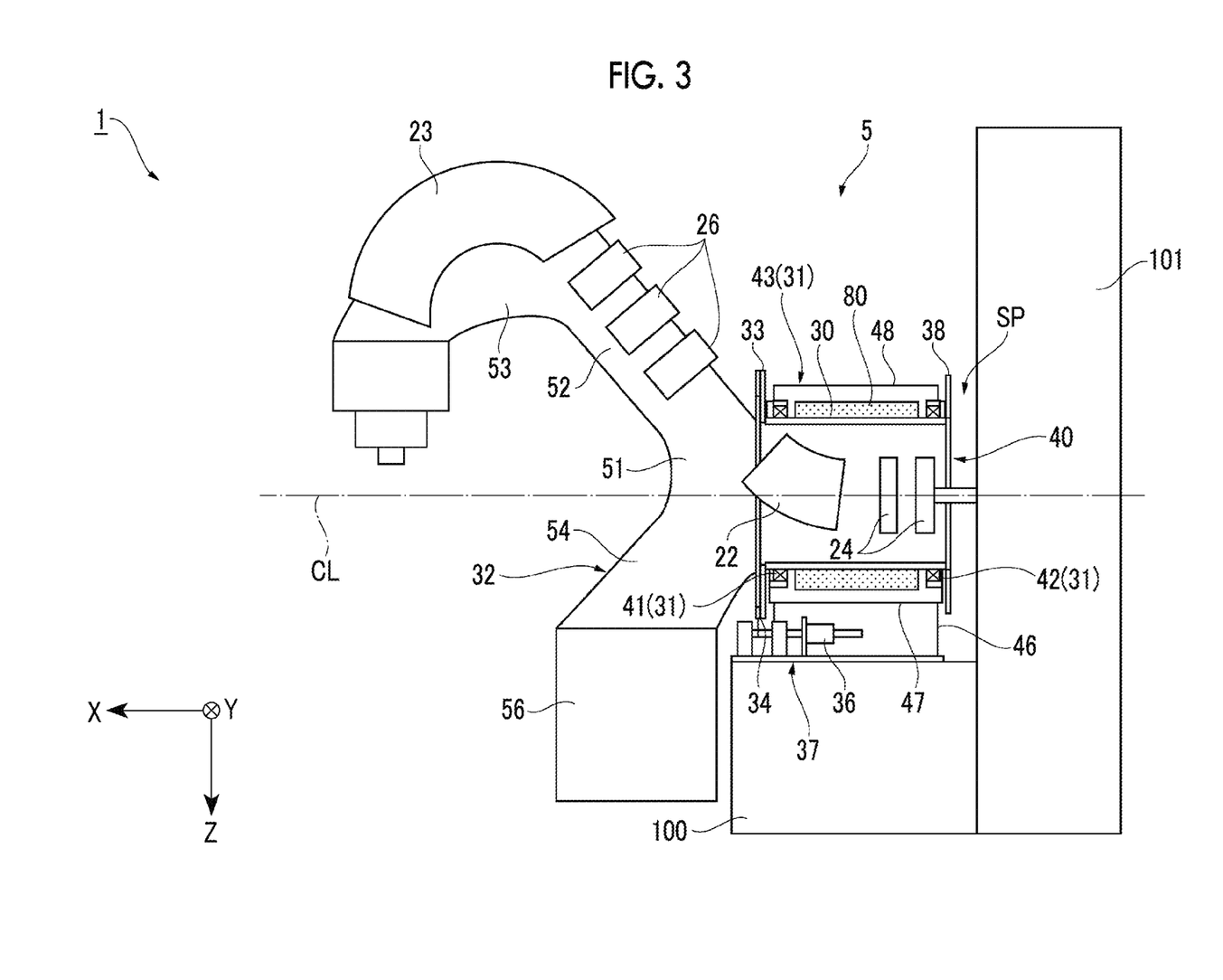
FIG. 3 is a schematic side view of the vicinity of the rotating gantry of the particle beam treatment apparatus.

FIG. 2 is a schematic perspective view of the vicinity of the rotating gantry 5 of the particle beam treatment apparatus 1 of FIG. 1. FIG. 3 is a schematic side view of the vicinity of the rotating gantry 5 of the particle beam treatment apparatus 1 of FIG. 1. In FIGS. 2 and 3, a tubular outer peripheral wall portion of the rotating gantry 5 is omitted, and the appearance of the electromagnet or a support frame is shown. In the following description, description will be made by using the terms "X axis direction", "Y axis direction", and "Z axis direction". The "Z axis direction" refers to the depth direction of irradiation of the particle beam from the irradiator 2. The "X axis direction" refers to one direction in a plane perpendicular to the Z axis direction, and a direction in which the rotation center line of the rotating gantry 5 extends. Of the rotating gantry 5, a side on which the treatment table 4 is installed is a positive side in the X axis direction. Further, the positive side in the X axis direction may be referred to as "front" and a negative side may be referred to as "rear". The "Y axis direction" refers to a direction perpendicular to the X axis direction in a plane perpendicular to the Z axis direction.

As shown in FIGS. 2 and 3, the rotating gantry 5 of the particle beam treatment apparatus 1 includes a rotary shaft 30, a support portion 31, and a support frame 32. In the following description, description will be made by using the state when the irradiator 2 is disposed directly above a center line CL as a reference.

The rotary shaft 30 is a hollow member inside which the electromagnet that controls the particle beam is disposed and which is provided so as to be rotatable by a power source. The rotary shaft 30 is rotated around the center line CL of the rotating gantry 5. The rotary shaft 30 is a cylindrical member extending in the front-rear direction along the center line CL. In the internal space of the rotary shaft 30, a quadrupole electromagnet 24 and the bending electromagnet 22 are disposed in order from the downstream side. The quadrupole electromagnet 24 is an electromagnet that controls the particle beam by focusing the particle beam. The bending electromagnet 22 is an electromagnet that controls the particle beam so as to deflect the direction of the particle beam transported along the center line CL in a direction inclined with respect to the center line CL.

The rotary shaft 30 has a monocoque structure. The rotary shaft 30 having a monocoque structure is a rotary shaft formed by making a single plate member into a cylindrical shape, unlike a rotary shaft having a frame structure formed by combining a plurality of frame members. Therefore, in the internal space of the rotary shaft 30, a wide space is secured without a frame for reinforcement or the like provided.

A drive disc 33 is provided at a front end portion of the rotary shaft 30. The drive disc is a flat plate-shaped annular member extending from the front end portion of the rotary shaft 30 to the outer peripheral side. As shown in FIG. 3, a drive chain 34 is wound around an outer peripheral edge portion of the drive disc 33. The drive chain 34 is connected to a winding device 37 including a power source 36. The winding device 37 is provided below the drive disc 33, and can rotate the drive disc 33 by winding or unwinding the drive chain 34. In this manner, the drive disc 33 is rotated, whereby the rotary shaft 30 is rotated. The rotary shaft 30 (that is, the irradiator 2) can rotate 360° around the center line CL. However, the rotatable angle of the rotary shaft 30 is not particularly limited, and may not necessarily be 360° rotatable.

A brake disc 38 is provided at a rear end portion of the rotary shaft 30. The brake disc 38 is a flat plate-shaped annular member extending from the rear end portion of the rotary shaft 30 to the outer peripheral side. The brake disc is a member that applies a braking force to the rotating rotary shaft 30 when a brake pad is pressed against the rotary shaft 30. As shown in FIG. 2, a space is provided in a region on the inner peripheral side of the brake disc 38. Further, the rear end portion of the rotary shaft 30 is also in an open state without being blocked. The space on the inner peripheral side of the brake disc 38 and an opening portion 40 of the rear end portion of the rotary shaft 30 communicate with each other. Therefore, the internal space of the rotary shaft 30 is open to the outside in a rear portion of the rotary shaft 30 (one end side in the direction along the rotary shaft 30).

The support portion 31 rotatably supports the rotary shaft 30. As shown in FIG. 3, in the present embodiment, the support portion 31 includes bearings 41 and 42 and a housing 43. The bearing 41 is an annular member that is provided on the front portion side of the rotary shaft 30 and that rotatably supports the rotary shaft 30. The bearing 42 is an annular member that is provided on the rear portion side (one end side) of the rotary shaft 30 and that rotatably supports the rotary shaft 30. The bearings 41 and 42 are provided on the surfaces of the rotary shaft 30 on the outer peripheral side.

The housing 43 is a box body that accommodates the rotary shaft 30. The housing 43 is fixed to a foundation portion 100 on the building side provided below the rotary shaft 30. The housing 43 supports the bearings 41 and 42 provided on the rotary shaft 30 from the outer peripheral sides, and fixes the positions of the bearings 41 and 42. With this, the rotary shaft 30 can rotate in a state of being supported by the housing 43 and the foundation portion 100 through the bearings 41 and 42.

As shown in FIG. 2, the housing 43 includes a base portion 46, a lower case 47, and an upper case 48. The base portion 46 is a portion that supports the lower case 47 and the upper case 48 from the lower side, and is a portion that is fixed to the foundation portion 100 (see FIG. 3). The lower case 47 accommodates the lower portion of the rotary shaft 30. The upper case 48 accommodates the upper portion of the rotary shaft 30. The upper case 48 includes a pair of side wall portions 48a extending in the vertical direction, a pair of inclined wall portions 48b inclined in the diagonal direction, and an upper wall portion 48c extending in the horizontal direction.

As shown in FIGS. 2 and 3, the support frame 32 is a frame structure that supports the irradiator 2. The support frame 32 is provided on the front side of the rotary shaft 30. The support frame 32 includes a connection portion 51, an inclined portion 52, a turn portion 53, and a counterweight attachment portion 54. The support frame 32 is not supported by a structure of the building. Therefore, the rotating gantry 5 has a cantilever support structure supported by the foundation portion 100 at the position of the rotary shaft 30.

The connection portion 51 is a portion connected to the front end portion of the rotary shaft 30. The connection portion 51 is fixed to the front end portion of the rotary shaft 30 at the position of the center line CL. The inclined portion 52 is a portion that extends in a state of being inclined diagonally upward toward the front side. The inclined portion 52 is connected to the upper side of the connection portion 51. A quadrupole electromagnet 26 that focuses the particle beam is provided in the inclined portion 52. The turn portion 53 is a portion that turns downward at the upper end part of the inclined portion 52. The irradiator 2 is provided at the tip part of the turn portion 53. In addition, the bending electromagnet 23 is provided in the turn portion. The bending electromagnet 23 bends the trajectory so as to make the particle beam, which is transported from the rotary shaft 30 through the quadrupole electromagnet 26, turn and transports the particle beam to the irradiator 2. The counterweight attachment portion 54 is a portion to which the counterweight 56 is attached. The counterweight attachment portion 54 extends so as to be inclined toward the side opposite to the inclined portion 52 with the center line CL interposed therebetween, that is, downward. The counterweight 56 is attached to the lower end part of the inclined portion 52. As described above, the counterweight 56 is provided on the side of the support frame 32 of the rotating gantry 5.

Here, the particle beam treatment apparatus 1 according to the present embodiment has a structure in which the hollow portion of the rotary shaft 30 is accessible to the worker. Next, the structure in which the hollow portion of the rotary shaft 30 is accessible will be described.

Figure 4:
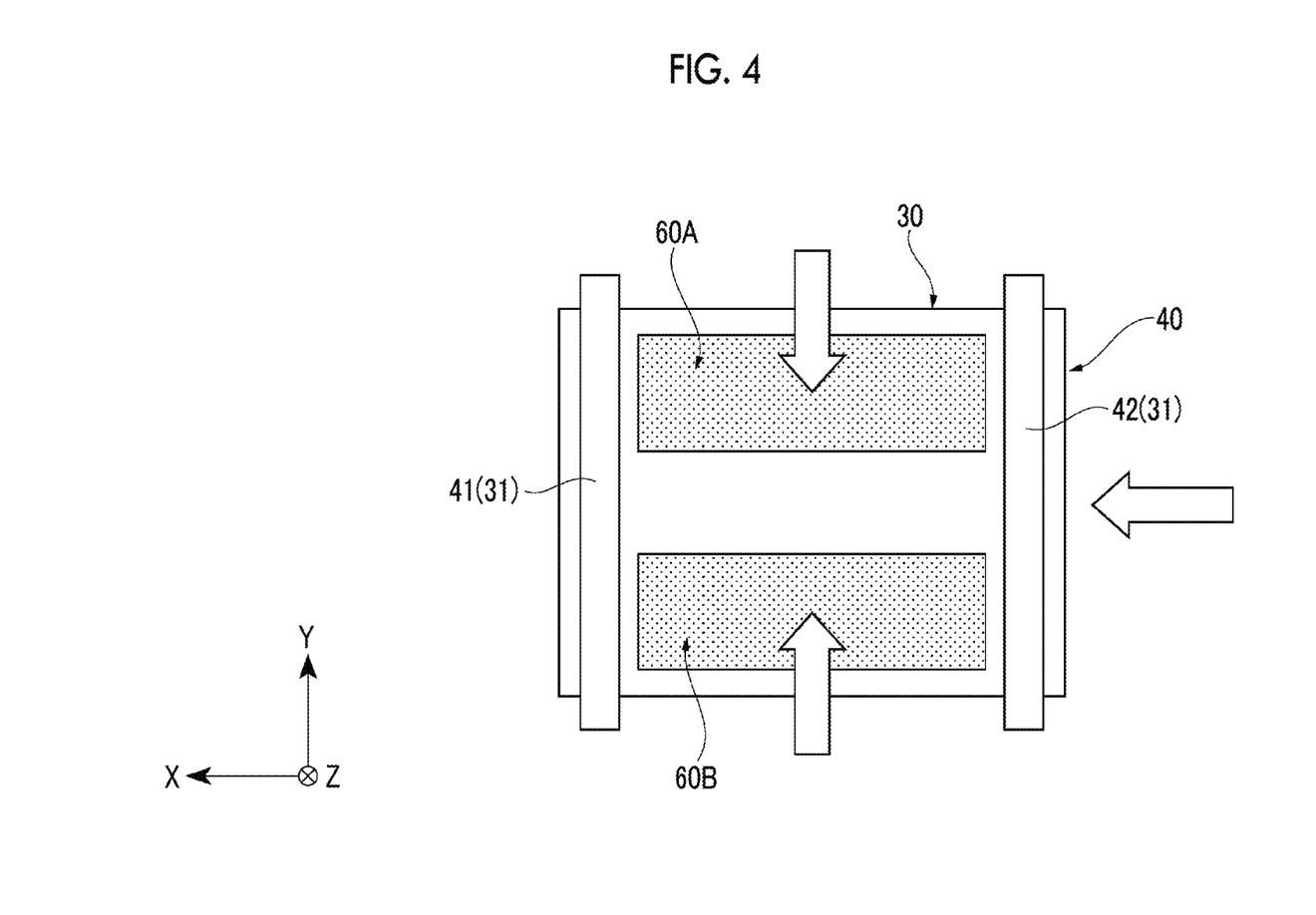
FIG. 4 is a schematic view of a rotary shaft as viewed from above.

FIG. 4 is a schematic view of the rotary shaft 30 as viewed from above. FIGS. 5A to 5D are schematic views of the rotary shaft 30 as viewed from the axial direction. As shown in FIGS. 4 and 5A to 5D, the rotary shaft 30 includes an opening portion 60 (first opening portion). The particle beam treatment apparatus 1 allows the hollow portion of the rotary shaft 30 to be accessible to the worker through the opening portion 60. In FIG. 4, the grayscale part corresponds to the opening portion 60. In the present embodiment, the rotary shaft 30 includes four opening portions 60A, 60B, 60C, and 60D formed at a constant pitch (here, 90° pitch). The shapes of the opening portions 60A, 60B, 60C, and 60D are not particularly limited, but in the present embodiment, the opening portions 60A, 60B, 60C, and 60D each form a rectangular shape so as to have a longitudinal direction in the X axis direction. In the X axis direction, the opening portions 60A, 60B, 60C, and 60D are formed in the region between the bearing 41 on the front side and the bearing 42 on the rear side. The pitch and number of the opening portion 60 are not particularly limited.

As shown in FIGS. 5A to 5D, the housing 43 includes an opening portion 70 (second opening portion). The particle beam treatment apparatus 1 allows the hollow portion of the rotary shaft 30 to be accessible to the worker through the opening portion 60 of the rotary shaft 30 and the opening portion 70 of the housing 43. In the present embodiment, the housing 43 includes the opening portion 70 provided at the position of the inclined wall portion 48b (see the grayscale part in FIG. 2). The opening portion 70 forms a rectangular shape so as to have a longitudinal direction in the X axis direction. The opening portion 60 of the rotary shaft 30 moves with the rotation of the rotary shaft 30. On the other hand, since the housing 43 is not rotated, the position of the opening portion 70 of the housing 43 is immovable. Therefore, in a case where the opening portion 60 of the rotary shaft 30 and the opening portion 70 of the housing 43 overlap with each other when viewed from the outside, the hollow portion of the rotary shaft 30 is accessible from the outside through the opening portions 60 and 70.

The sizes of the opening portions 60 and 70 for making the hollow portion of the rotary shaft 30 accessible will be described. The minimum portions of the opening portions 60 and 70 may each have a dimension of 12 inches or more. There are standards that define an opening with the minimum portion having a dimension of 12 inches or more as an opening where people may fall on floors, gantry, paved roads, material storage areas, or the like (for example, US OSHA Standards Part No. 1910 Occupational Safety and Health Standards). That is, it can be said that the dimension of the minimum portion is secured to be 12 inches or more so that the worker can pass through the opening portions 60 and 70. Further, the dimensions of the minimum portions of the opening portions 60 and 70 may each be 24 inches or more. By providing twice the opening width of 12 inches, smooth access is possible. In a case of a rectangular opening portion, the dimension of the minimum portion means the dimension in the lateral direction. In addition, the dimension of the minimum portion means the dimension of the short axis in a case of an ellipse, and means the dimension of the portion where the distance between the facing edges is the shortest in a case of a polygonal shape.

Figure 6:
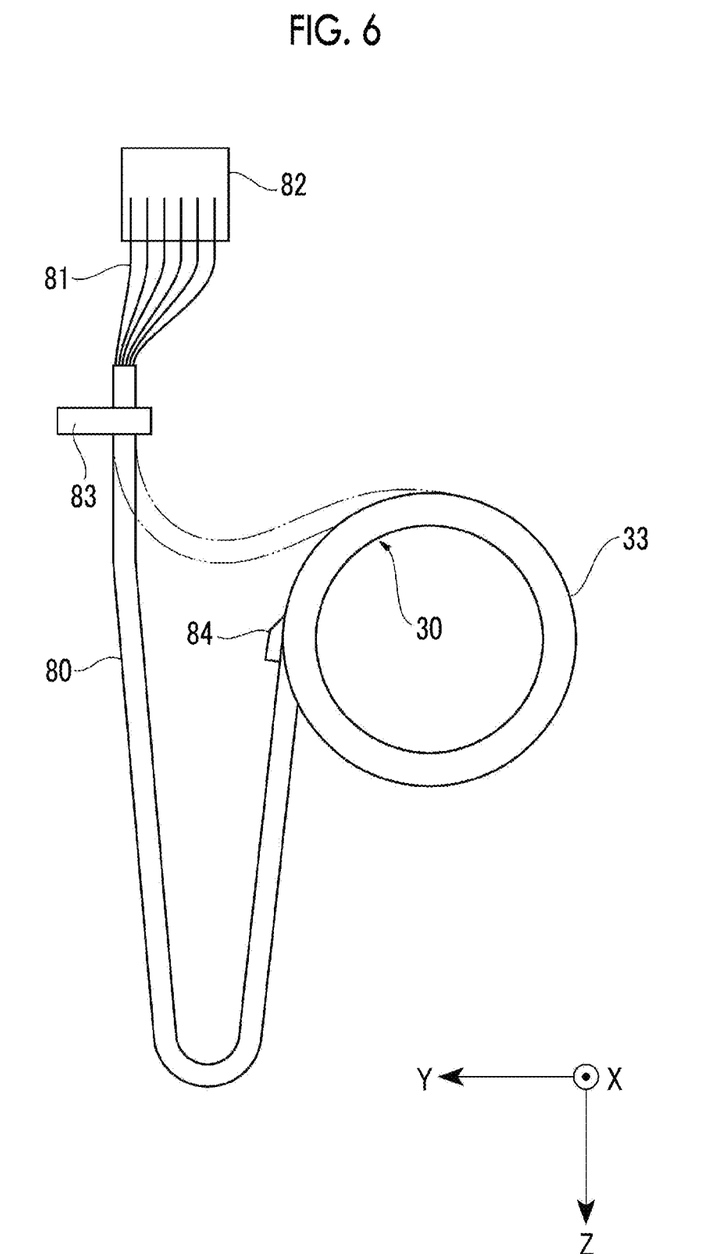
FIG. 6 is a schematic view of the rotary shaft as viewed from the axial direction.

Here, as shown in FIG. 6, there is a case where the particle beam treatment apparatus 1 includes a cableveyor 80 (registered trademark, cable accommodation body) that accommodates a cable 81 connected to the electromagnet. The cableveyor 80 is attached so as to be windable around the rotary shaft 30, and is drawn out of one side (the positive side in the Y axis direction) when viewed from the axial direction in which the center line CL of the rotary shaft 30 extends. The cable 81 is drawn out of a device 82 provided at a position on the positive side of the rotary shaft 30 in the Y axis direction, and is guided to the rotary shaft 30 in a state of being bundled by the cableveyor 80. One end portion of the cableveyor 80 is fixed by a fixation portion 83 disposed below the device 82. Then, the cableveyor 80 is attached to the rotary shaft 30 through an attachment portion 84 in a state of hanging down between the fixation portion 83 and the rotary shaft 30. The cable 81 enters the hollow portion of the rotary shaft 30 from the position of the attachment portion 84 and is connected to each electromagnet. When the rotary shaft 30 is rotated, the end portion of the cableveyor 80 is also rotated together with the attachment portion 84. With this, the cableveyor 80 is wound around the outer peripheral surface of the rotary shaft 30. In this case, the hanging-down portion of the cableveyor 80 between the fixation portion 83 and the rotary shaft 30 becomes shorter (see the imaginary line in FIG. 6).

The cableveyor 80 has a flat shape in a width direction and is wound so as to occupy a predetermined region in the axial direction of the rotary shaft 30 (see the grayscale region in FIG. 3). Therefore, a structure is adopted in which the opening portion 60 is not blocked by the cableveyor 80. Specifically, a configuration is adopted in which the cableveyor 80 is drawn out of only one side (positive side in the Y axis direction) and is not drawn out of the other side (negative side in the Y axis direction) when viewed from the axial direction in which the center line CL of the rotary shaft 30 extends. With this, a configuration is adopted in which the hollow portion of the rotary shaft 30 is easily accessed from the side (negative side in the Y axis direction) opposite to the draw-out side of the cableveyor 80. Further, as shown in FIGS. 5A to 5D, the opening portion 70A is formed in the housing 43 on the side opposite to the draw-out side of the cableveyor 80 when viewed from the axial direction. In the present embodiment, the opening portion 70B is also formed in the housing 43 on the draw-out side of the cableveyor 80.

Figure 5A:
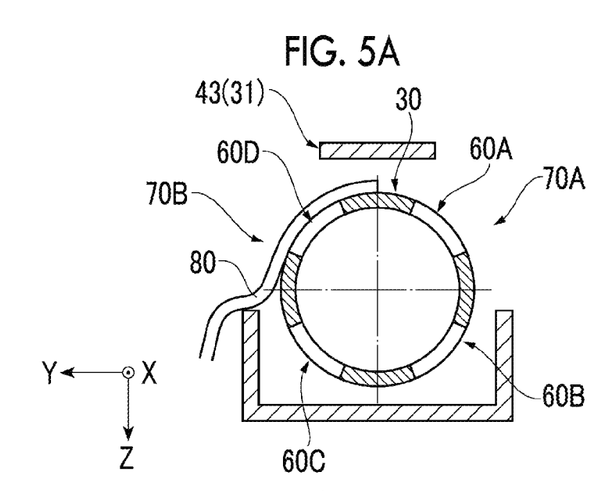
FIGS. 5A to 5D are schematic views of the rotary shaft as viewed from an axial direction.
Figure 5B:
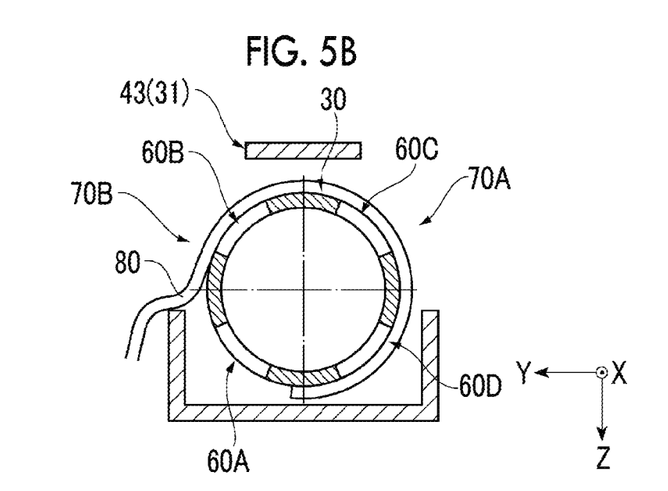
Figure 5C:
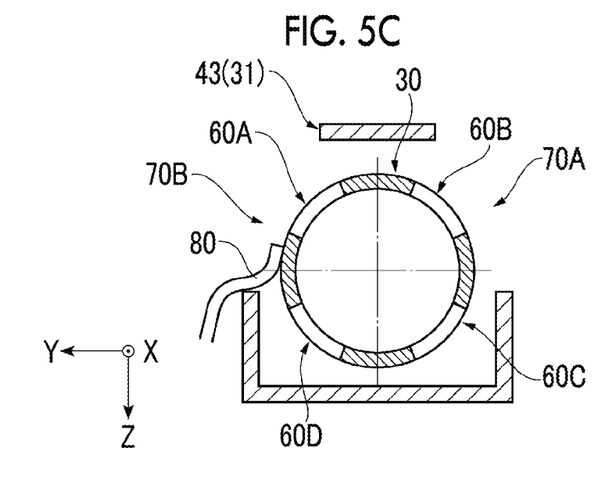
Figure 5D:
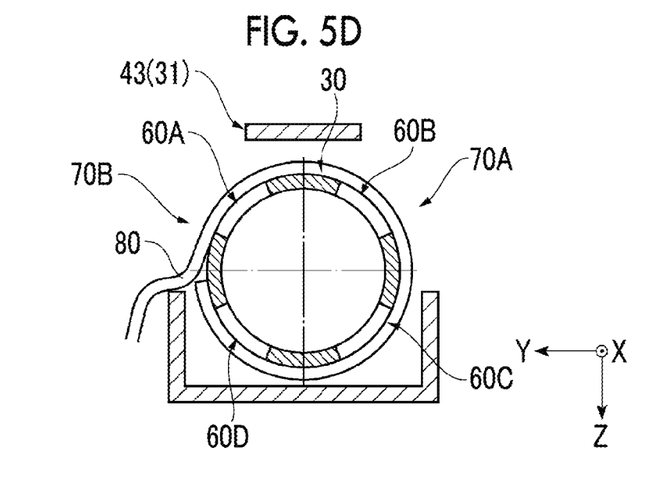

Next, the relationship between the rotation angle of the rotary shaft 30 and the winding mode of the cableveyor 80 will be described with reference to FIGS. 5A to 5D. Here, for ease of illustration, the state shown in FIG. 5C is assumed to be a state in which the rotation angle is 0°. In the state where the rotation angle is 0°, the attachment position of the cableveyor 80 is disposed at the end portion on the positive side in the Y axis direction, and the opening portion 60A overlaps with the opening portion 70B in a state of being not blocked, and the opening portion 60B overlaps with the opening portion 70A in a state of being not blocked. In this case, the hollow portion of the rotary shaft 30 is accessible from the opening portions 60A and 70B and the opening portions 60B and 70A. As shown in FIG. 5A, in a case where the rotation angle of the rotary shaft 30 becomes 90°, the opening portion 60D in a state of being blocked by the cableveyor 80 is disposed at the position of the opening portion 70B. In this case, the opening portion 60A overlaps with the opening portion 70A in a state of being not blocked. In this case, the hollow portion of the rotary shaft 30 is accessible from the opening portions 60A and 70A. As shown in FIG. 5B, in a case where the rotation angle of the rotary shaft 30 becomes 270°, the opening portion 60B in a state of being blocked by the cableveyor 80 is disposed at the position of the opening portion 70B, and the opening portion 60C in a state of being blocked by the cableveyor 80 is disposed at the position of the opening portion 70A. As shown in FIG. 5D, in a case where the rotation angle of the rotary shaft 30 becomes 360°, the opening portion 60A in a state of being blocked by the cableveyor 80 is disposed at the position of the opening portion 70B, and the opening portion 60B in a state of being blocked by the cableveyor 80 is disposed at the position of the opening portion 70A. Therefore, in the cases of FIGS. 5B and 5D at the time of maintenance, the rotary shaft 30 is rotated so as to be in the state shown in FIG. 5A or 5C, so that the hollow portion of the rotary shaft 30 is accessible.

Further, an opening portion 40 is provided on the rear portion (one end side) of the rotary shaft 30 to allow the hollow portion of the rotary shaft 30 to be accessible to the worker from the rear portion side (one end side). As described above, the internal space of the rotary shaft 30 is open to the outside by the opening portion 40 (see FIG. 2) of the rear end portion of the rotary shaft 30, at the rear portion of the rotary shaft 30. Further, as shown in FIG. 3, a gap SP is provided between the opening portion 40 of the rear end portion of the rotary shaft 30 and a wall portion 101 of the building on the rear side of the rotating gantry 5. In the gap SP, a dimension that the worker can pass through is secured. Therefore, the worker turns toward the gap SP and enters the rear end portion of the rotary shaft 30, so that the hollow portion of the rotary shaft 30 is accessible to the worker from the opening portion 40. Further, the bearing 42 is provided on the rear portion side of the rotary shaft 30. That is, the rear portion of the rotary shaft 30 has a support structure supported by the bearing 42 in which a large space is provided on the inner peripheral side, not a support structure that blocks the opening portion 40 or obstructs passage from the opening portion 40. Therefore, the hollow portion of the rotary shaft 30 is accessible to the worker from the inner peripheral side of the bearing 42.

Next, the operation and effects of the particle beam treatment apparatus 1 according to the present embodiment will be described.

The particle beam treatment apparatus 1 includes the rotary shaft 30 including a hollow portion, and the electromagnets 22 and 24 that control the particle beam in the hollow portion, the rotary shaft being rotatable by the power source 36. Since the rotary shaft 30 has a hollow structure, a space of a predetermined size is provided in the hollow portion of the rotary shaft. Therefore, the electromagnets 22 and 24 can be disposed in the space provided in the hollow portion of the rotary shaft 30. The rotary shaft 30 includes the opening portion 60. The particle beam treatment apparatus 1 allows the hollow portion of the rotary shaft 30 to be accessible to the worker through the opening portion 60. Therefore, the hollow portion of the rotary shaft 30 is accessible to the worker through the opening portion 60 to allow the worker to perform maintenance of the electromagnets 22 and 24 in the space secured in the hollow portion of the rotary shaft 30. Consequently, the maintenability of the electromagnets 22 and 24 in the rotary shaft 30 can be improved.

In a case of an assembly type rotary shaft, it is necessary to remove the rotary shaft at the time of maintenance. However, in this case, it is difficult to return to the state before maintenance, and there is a possibility that problems such as deviation of the particle beam may occur. On the other hand, in the present embodiment, since the worker can perform the maintenance in the hollow portion of the rotary shaft 30, the above problems can be avoided.

The rotary shaft 30 may have a monocoque structure. In this case, it is possible to secure a wider space in the hollow portion of the rotary shaft 30 as compared with the rotary shaft of the frame structure or the like. In addition, it is easier to form the opening portion 60 with respect to the rotary shaft 30.

The support portion 31 may include the housing 43 that accommodates the rotary shaft 30, the housing 43 including the opening portion 70, the hollow portion of the rotary shaft 30 being accessible to the worker through the opening portion 60 and the opening portion 70. In this case, the worker passes through the opening portion 70 even in a case where the housing 43 is provided on the outer side of the rotary shaft 30, whereby the hollow portion of the rotary shaft 30 is accessible to the worker.

The particle beam treatment apparatus 1 may further include the cableveyor 80 that accommodates the cable 81 connected to the electromagnets 22 and 24, in which the cableveyor 80 may be attached so as to be windable around the rotary shaft 30, and may be drawn out of one side of the rotary shaft 30 when viewed from the axial direction in which the center line CL of the rotary shaft 30 extends. In this case, the rotary shaft 30 is set to have a specific rotation angle (for example, see FIGS. 5A and 5C), so that it is possible to avoid the cableveyor 80 to access the hollow portion of the rotary shaft 30.

The support portion 31 may include the housing 43 that accommodates the rotary shaft 30, and the opening portion 70 may be formed in the housing 43 on the side opposite to the draw-out side of the cableveyor 80 when viewed from the axial direction. In this case, the hollow portion of the rotary shaft 30 is easily accessible from the side opposite to the draw-out side of the cableveyor 80 through the opening portion 70.

The first opening portion is provided on one end side of the rotary shaft 30 to allow the hollow portion of the rotary shaft 30 to be accessible to the worker from the one end side. In this case, the hollow portion of the rotary shaft 30 is accessible to the worker from the rear portion side of the rotary shaft 30 to allow the worker to perform maintenance of the electromagnets 22 and 24.

The particle beam treatment apparatus 1 may further include a bearing 42 provided on the one end side of the rotary shaft 30, the hollow portion of the rotary shaft 30 being accessible to the worker from the inner peripheral side of the bearing 42. The rotary shaft 30 is supported by using the bearing 42 in which a large space is provided on the inner peripheral side, so that the support structure on the one end side of the rotary shaft 30 can restrain the opening from being blocked. With this, the hollow portion of the rotary shaft 30 is accessible to the worker from the inner peripheral side of the bearing 42 without the obstruction of the passage.

The particle beam treatment apparatus 1 may further include the irradiator 2 that irradiates the irradiation target with the particle beam; and the support frame 32 that supports the irradiator 2, in which the counterweight 56 may be provided on the side of the support frame 32. In this case, since the counterweight 56 is disposed at a position that does not obstruct the worker's access to the hollow portion of the rotary shaft 30, the hollow portion of the rotary shaft 30 is easily accessed.

The present invention is not limited to the above-described embodiment.

Figure 7:
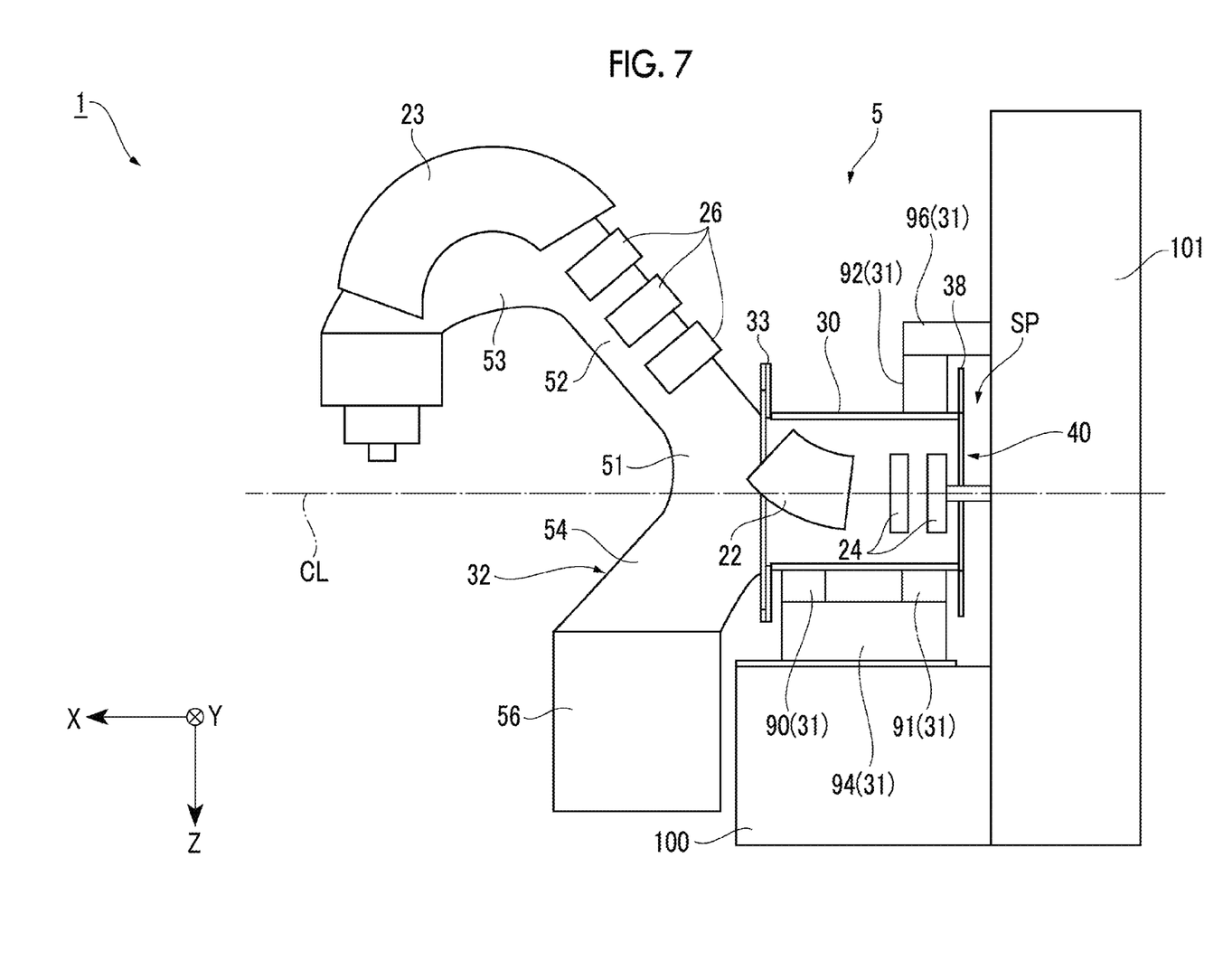
FIG. 7 is a schematic side view of the vicinity of a rotating gantry of a particle beam treatment apparatus according to a modification example.

The structure of the support portion 31 that supports the rotary shaft 30 is not limited to the above-described embodiment. For example, the structure shown in FIG. 7 may be adopted. The support portion 31 shown in FIG. 7 includes roller members 90, 91, and 92. The roller member 90 is capable of applying a rotation driving force to the rotary shaft 30 and supporting the own weight of the rotary shaft. The roller member 90 is provided below the front portion side of the rotary shaft 30. The roller member 91 is capable of supporting the own weight of the rotary shaft. The roller member 91 is provided below the rear portion side of the rotary shaft 30. The roller members 90 and 91 are supported from below by a base portion 94 provided on the foundation portion 100. The roller member 92 is capable of restraining the uplift of the rotary shaft 30. The roller member 92 is provided above the rear portion side of the rotary shaft 30. The roller member 92 is supported from above by a pressing portion 96. In this case, bearings as shown in FIG. 3 may not necessarily be provided for the rotary shaft 30. Accordingly, it is possible to omit the housing. Consequently, it is possible to restrain a structure from being provided around the rotary shaft 30, so that the hollow portion of the rotary shaft 30 is easily accessed. The structure in which the housing is provided is not excluded even in a case where the roller member 90 is used.

The housing 43 may have either a monocoque structure or a frame structure. Further, the rotary shaft 30 may be hollow and may not necessarily have a monocoque structure.

The structure of the rotating gantry 5 may be appropriately modified without departing from the gist of the present invention.

It should be understood that the invention is not limited to the above-described embodiment, but may be modified into various forms on the basis of the spirit of the invention. Additionally, the modifications are included in the scope of the invention.

What is claimed is:

1. A particle beam treatment apparatus that irradiates an irradiation target with a particle beam, the apparatus comprising:
    a rotary shaft including a hollow portion;
    an electromagnet that controls the particle beam in the hollow portion, the rotary shaft being rotatable by a power source;
    a support portion that rotatably supports the rotary shaft; and
    an irradiator that is connected to one end of the rotary shaft and irradiates the irradiation target with the particle beam; and
    a first bearing provided on the other end of the rotary shaft, the hollow portion being accessible to a worker through an inner peripheral side of the first bearing,
    wherein the rotary shaft includes a first opening portion provided on the other end of the rotary shaft.

2. The particle beam treatment apparatus according to claim 1,
    wherein the rotary shaft has a monocoque structure.

3. The particle beam treatment apparatus according to claim 1,
    wherein the support portion includes a housing that accommodates the rotary shaft, the housing including a second opening portion, the hollow portion being accessible to the worker through the first opening portion and the second opening portion.

4. The particle beam treatment apparatus according to claim 1,
    wherein the support portion includes a second bearing that rotatably supports the rotary shaft, and
    the second bearing is provided on one end side that is closer to the irradiator.

5. The particle beam treatment apparatus according to claim 1,
    wherein the support portion includes roller members that apply a rotation driving force to the rotary shaft.

6. The particle beam treatment apparatus according to claim 5, wherein the roller members are provided below one end side in a direction along the rotary shaft, below the other end side in the direction along the rotary shaft, and above the other end side of the rotary shaft.

7. The particle beam treatment apparatus according to claim 1, further comprising:
a cable accommodation body that accommodates a cable connected to the electromagnet,
wherein the cable accommodation body is attached so as to be windable around the rotary shaft, and is drawn out of one side of the rotary shaft when viewed from an axial direction in which a center line of the rotary shaft extends.

8. The particle beam treatment apparatus according to claim 7,
wherein the cable accommodation body has a substantially flat shape in the axial direction.

9. The particle beam treatment apparatus according to claim 7,
wherein the support portion includes a housing that accommodates the rotary shaft, and
a second opening portion is formed in the housing on a side opposite to a draw-out side of the cable accommodation body when viewed from the axial direction.

10. The particle beam treatment apparatus according to claim 1, further comprising:
a support frame that is connected to the one end of the rotary shaft and supports the irradiator.

11. The particle beam treatment apparatus according to claim 10,
wherein the support frame is formed of a connection portion connected to the one end of the rotary shaft, an inclined portion connected to an upper side of the connection portion, a turn portion turning downward in the inclined portion, and a counterweight attachment portion to which a counterweight is attached.

12. The particle beam treatment apparatus according to claim 11,
wherein electromagnets are provided in the inclined portion and the turn portion.

13. The particle beam treatment apparatus according to claim 1,
wherein the first opening portion is provided on a side surface of the rotary shaft.

14. The particle beam treatment apparatus according to claim 1,
wherein the first opening portion is provided on at least one of a side surface of the rotary shaft and the other end of the rotary shaft.

* * * * *